(12) United States Patent  
Narwankar et al.

(10) Patent No.: US 9,305,838 B2  
(45) Date of Patent: Apr. 5, 2016

(54) BEOL INTERCONNECT WITH CARBON NANOTUBES

(75) Inventors: Pravin K. Narwankar, Sunnyvale, CA (US); Joe Griffith Cruz, San Jose, CA (US); Arvind Sundarrajan, San Jose, CA (US); Murali Narasimhan, San Jose, CA (US); Subbalakshmi Sreekala, Sunnyvale, CA (US); Victor Pushparaj, Sunnyvale, CA (US)

(73) Assignee: Applied Materials, Inc., Santa Clara, CA (US)

( * ) Notice: Subject to any disclaimer, the term of this patent is extended or adjusted under 35 U.S.C. 154(b) by 298 days.

(21) Appl. No.: 13/601,963

(22) Filed: Aug. 31, 2012

(65) Prior Publication Data

US 2013/0228933 A1     Sep. 5, 2013

Related U.S. Application Data

(60) Provisional application No. 61/529,699, filed on Aug. 31, 2011.

(51) Int. Cl.
*H01L 29/41* (2006.01)
*H01L 21/768* (2006.01)
(Continued)

(52) U.S. Cl.
CPC ............ *H01L 21/76877* (2013.01); *A61K 8/46* (2013.01); *A61K 8/8182* (2013.01);
(Continued)

(58) Field of Classification Search
CPC .................... H01L 21/02606; H01L 29/0669; H01L 29/413; H01L 2221/1094
See application file for complete search history.

(56) References Cited

U.S. PATENT DOCUMENTS 7,094,679 B1      8/2006   Li et al.
2004/0222081 A1*  11/2004  Tour et al. ............... 204/157.15
(Continued)

FOREIGN PATENT DOCUMENTS

JP      2010-186858 A      8/2010
KR   10-2008-0128988 A   12/2006
(Continued)

OTHER PUBLICATIONS

International Search Report and Written Opinion issued Feb. 26, 2013 for PCT/US2012/053202.
(Continued)

*Primary Examiner* — Evan Pert
*Assistant Examiner* — Leslie Pilar Cruz
(74) *Attorney, Agent, or Firm* — Pillsbury Winthrop Shaw Pittman LLP

(57) ABSTRACT

An integrated circuit with BEOL interconnects may comprise: a substrate including a semiconductor device; a first layer of dielectric over the surface of the substrate, the first layer of dielectric including a filled via for making electrical contact to the semiconductor device; and a second layer of dielectric on the first layer of dielectric, the second layer of dielectric including a trench running perpendicular to the longitudinal axis of the filled via, the trench being filled with an interconnect line, the interconnect line comprising cross-linked carbon nanotubes and being physically and electrically connected to the filled via. Cross-linked CNTs are grown on catalyst particles on the bottom of the trench using growth conditions including a partial pressure of precursor gas greater than the transition partial pressure at which carbon nanotube growth transitions from a parallel carbon nanotube growth mode to a cross-linked carbon nanotube growth mode.

15 Claims, 9 Drawing Sheets

(51) Int. Cl.
- *A61Q 9/04* (2006.01)
- *H01L 23/538* (2006.01)
- *A61K 8/46* (2006.01)
- *A61K 8/81* (2006.01)
- *B82Y 40/00* (2011.01)

(52) U.S. Cl.
CPC ........... *A61Q 9/04* (2013.01); *H01L 21/76843* (2013.01); *H01L 23/5384* (2013.01); *A61K 2800/884* (2013.01); *B82Y 40/00* (2013.01); *H01L 29/413* (2013.01); *H01L 2924/0002* (2013.01); *Y10S 977/742* (2013.01)

(56) References Cited

U.S. PATENT DOCUMENTS

| | | |
|---|---|---|
| 2005/0129939 A1 | 6/2005 | Shigematsu et al. |
| 2006/0091557 A1* | 5/2006 | Sakamoto et al. ............ 257/774 |
| 2008/0197513 A1 | 8/2008 | Restaino et al. |
| 2011/0100955 A1 | 5/2011 | Pushparaj et al. |
| 2011/0186775 A1* | 8/2011 | Shah et al. ............... 252/182.32 |

FOREIGN PATENT DOCUMENTS

| | | |
|---|---|---|
| KR | 10-2008-0089243 A | 10/2008 |
| KR | 10-2009-0057089 A | 6/2009 |

OTHER PUBLICATIONS

Chai, Y., Chan P.C.H., Fu, Y. Chuang, Y.C., Liu, C.Y., "Copper/Carbon Nanotube Composite Interconnect for Enhanced Electromigration Resistance," 2008 Electronic Components and Technology Conference, pp. 412-420.

Chen, F., Ajay, J., Stojanović, V., Chandrakasan, A., "Scaling and Evaluation of Carbon Nanotube Interconnects for VLSI Applications," Nano-Net '07, Sep. 24-26, 2007, Catania, Italy.

Chai, Y., Zhang, K., Zhang, M., Chan, P.C.H., Yuen, M.M.F., "Carbon Nanotube/Copper Composites for Via Filling and Thermal Management," 2007 Electronic Components and Technology Conference, pp. 1224-1229.

Banerjee, K., and Srivastava, N., "Are Carbon Nanotubes the Future of VLSI Interconnections?" DAC 2006, Jul. 24-28, 2006, San Francisco, California.

Wolf, S., "Introduction to Dual-Damascene Interconnect Processes," Excerpt from Chapter 15.4 from Silicon Processing for the VLSI Era, vol. 4, pp. 674-679.

* cited by examiner

Process Flow for Single Damascene up US 9,305,838 B2

BEOL INTERCONNECT WITH CARBON NANOTUBES

CROSS-REFERENCE TO RELATED APPLICATIONS

This application claims the benefit of U.S. Provisional Application No. 61/529,699 filed Aug. 31, 2011, incorporated herein by reference in its entirety.

FIELD OF THE INVENTION

The present invention relates generally to methods for fabricating BEOL interconnects comprising carbon nanotubes, and equipment for high volume manufacturing of said interconnects.

BACKGROUND OF THE INVENTION

As the line widths of BEOL (back-end-of-line) interconnects for semiconductor integrated circuit devices continue to shrink, the interconnect line resistance increases. Line resistance for interconnects is important since it affects the transmission speed of signals along the interconnects and needs to be kept sufficiently low so as not to negatively impact signal transmission speed. The increase in line resistance with reducing interconnect line width becomes a problem for achieving sub-2x copper BEOL interconnects. There is a need for BEOL interconnects with reduced resistivity to achieve the desired line resistances for sub-2x BEOL interconnects. Furthermore, formation of interconnects with a reduced resistivity BEOL interconnect material must be integratable into a high volume manufacturing process, for which suitable deposition tools need to be available.

SUMMARY OF THE INVENTION

Embodiments of the present invention provide lower resistivity materials than electrodeposited copper for forming BEOL interconnect lines, and also for vias. The materials are CNT composites with metals or low k dielectrics. According to embodiments of the present invention, the CNTs, as deposited, are cross-linked, thus providing good signal conduction along the interconnect lines in a direction perpendicular to the general growth direction of the CNTs.

According to aspects of the invention, a method of fabricating a BEOL interconnect line may comprise: providing a substrate including a semiconductor device, a first layer of dielectric over the surface of the substrate and a second layer of dielectric on the first layer of dielectric, wherein the first layer of dielectric includes a filled via making electrical contact to the semiconductor device and the second layer of dielectric including an interconnect trench running perpendicular to the longitudinal axis of the filled via and exposing the filled via; depositing catalyst particles over the surface of the second layer of dielectric and the surfaces of said first layer of dielectric and the filled via exposed by the trench; growing cross-linked CNTs on the catalyst coated surfaces; depositing metal or low-k dielectric in the void space between the cross-linked CNTs; and removing excess material from the surface of the second layer of dielectric, leaving filled trenches with low line resistance. Prior to depositing the catalyst particles, thin films of Ta/TiN may be deposited on the surface of the second layer of dielectric and the bottom of the trench. The growing cross-linked CNTs may utilize hot wire chemical vapor deposition (HWCVD) with precursor gas pressure tuned for cross-linked growth. The depositing metal may include electrodeposition of Cu or CVD of metals such as W or Co. The depositing low-k dielectric may include HWCVD of polytetrafluoroethylene (PTFE). The removal of excess material may include chemical mechanical polishing.

Some embodiments of the present invention include dual damascene deposition, wherein the vias are also filled during the process of filling trenches with CNT composites.

Further embodiments of the present invention include cluster and in-line tools configured for the BEOL process with CNT composites.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF THE PREFERRED EMBODIMENTS

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

Figure 1:
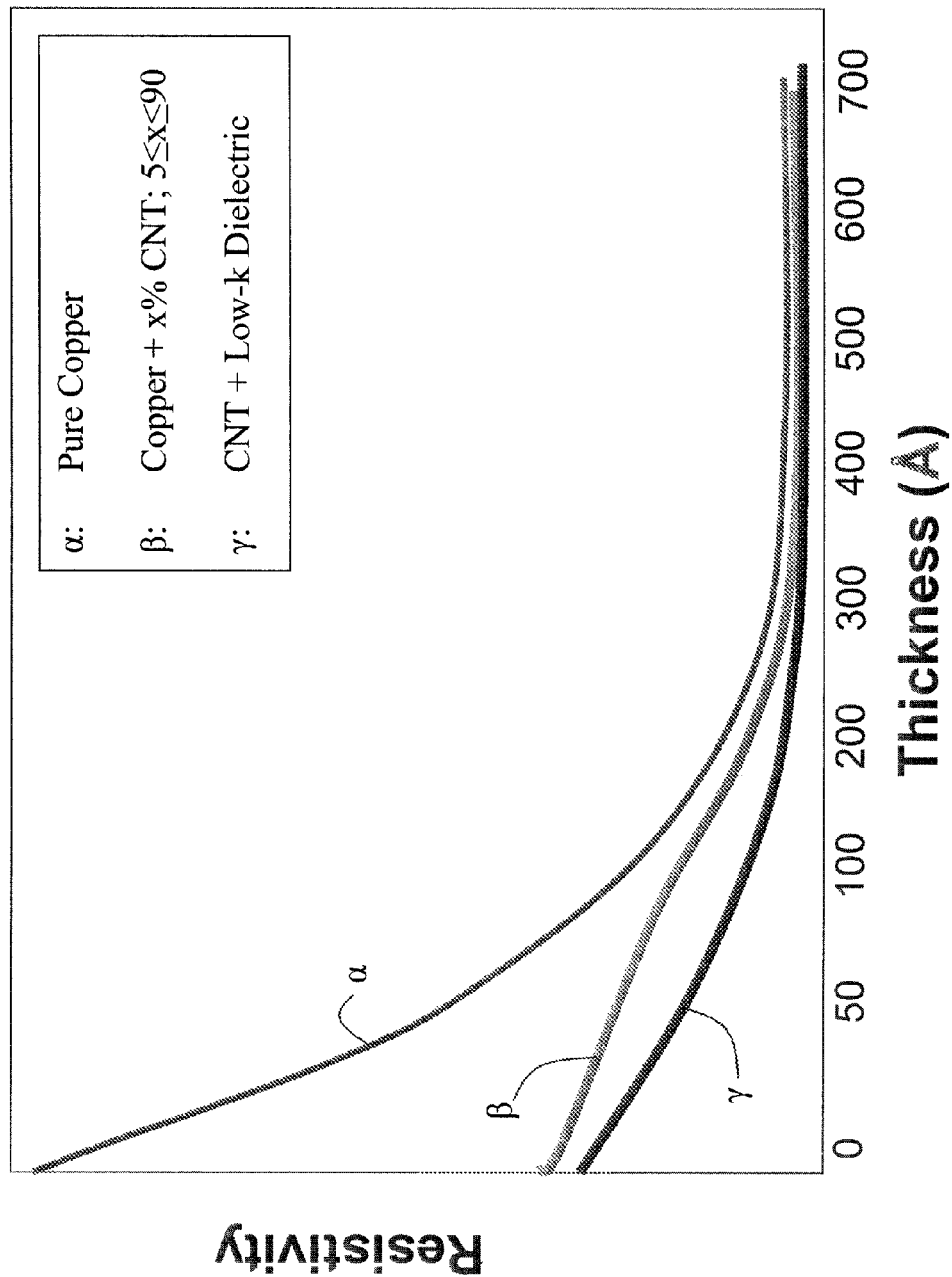
FIG. 1 shows a graph of resistivity against thickness for interconnect lines with various compositions, according to some embodiments of the present invention.

FIG. 1 shows plots of material resistivity against interconnect line thickness for various materials: pure copper; copper+x % CNT, where 5≤x≤90; CNT+low-k dielectric. With decrease in via opening or interconnect line width for BEOL interconnects, the line resistance increases. It is apparent from the graph that there is a distinct resistivity advantage with the CNT composite materials for roughly 100 Angstroms and below—for technology nodes at 2× and beyond the Cu interconnect may advantageously be replaced by CNT composites such as CNT/Cu or CNT/low-k dielectric.

Carbon nanotubes (CNTs) have electrical and mechanical properties that make them attractive for integration into a wide range of electronic devices, including semiconductor devices. Carbon nanotubes are nanometer-scale cylinders with walls formed of graphene—single atom thick sheets of graphite. Nanotubes may be either single-walled (cylinder wall composed of a single sheet of graphene, referred to as SWNTs) or multi-walled (cylinder wall composed of multiple sheets of graphene, referred to as MWNTs). Nanotubes have diameters as small as one nanometer, for a SWNT, and length to diameter ratios of the order of $10^2$-$10^5$. Carbon nanotubes can have either metallic or semiconducting electrical properties which make them suitable for integration into a variety of devices and processes, such as BEOL interconnects for semiconductor integrated circuits.

Figure 2:
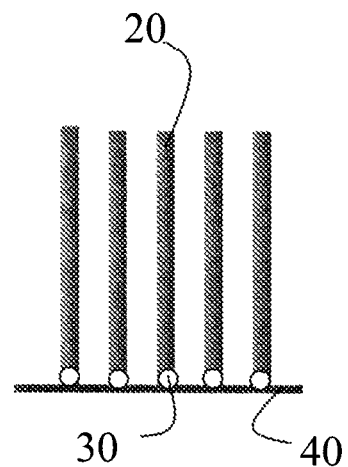
FIG. 2 shows a representation of CNTs grown under first conditions to form relatively parallel tubes, according to some embodiments of the present invention.
Figure 3:
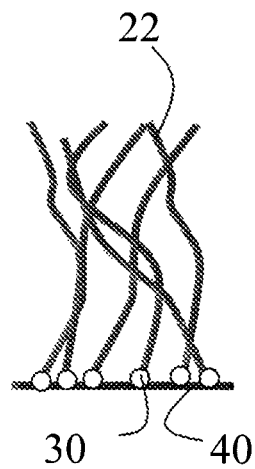
FIG. 3 shows a representation of CNTs grown under second conditions to form interconnected tubes, according to some embodiments of the present invention.

Carbon nanotubes can be grown using a variety of techniques including arc discharge, laser ablation and chemical vapor deposition (CVD), including hot wire CVD (HWCVD). The CNTs are grown on catalyst particles, which generally are heat activated. The catalyst material may be a transition metal such as Co, Ni, and Fe, or a transition metal alloy such as Fe—Ni, Co—Ni and Mo—Ni. The catalyst particles are only 10's or 100's of Angstroms in diameter and are deposited by processes which may include PVD, CVD and ALD. Underlayers for the catalyst of thin films, such as Ta/TiN, may also be used. CNT precursor compounds such as xylene and ethanol, or mixtures of such compounds may be used. FIGS. 2 and 3 show examples of CNTs 20, 22 grown on catalyst particles 30, the catalyst particles having been formed on underlayers 40.

CNTs may be grown with varying morphologies depending on the process conditions. FIG. 2 is a representation of CNTs grown under process conditions to form relatively parallel tubes 20, which grow roughly perpendicular to the deposition surface; whereas FIG. 3 shows a representation of CNTs grown under process conditions to form cross-linked tubes 22. According to some embodiments of the present invention, CVD deposition of CNTs under higher pressure is used to form cross-linked CNTs. Desirable conditions for growth of cross-linked CNTs are determined for a particular deposition chamber by increasing the precursor gas partial pressure until cross-linked CNTs are being formed. As an example, deposition of cross-linked MWCNTs has been achieved using HWCVD at a temperature of less than 500° C. in a chamber on an Applied Materials Endura™ platform; the precursor gas partial pressure was chosen to provide cross-linked CNTs after running a chamber calibration as described above. Consequently, growing cross-linked carbon nanotubes comprises selecting growth conditions including a partial pressure of precursor gas greater than the transition partial pressure at which carbon nanotube growth transitions from a parallel carbon nanotube growth mode to a cross-linked carbon nanotube growth mode.

The electrical conductivity of the CNTs 20 shown in FIG. 2 is much higher in the vertical direction (along the length of the tubes), than it is perpendicular to the length of the tubes. However, for the cross-linked CNTs 22 shown in FIG. 3 the electrical conductivity does not show any marked directional dependence. Being able to control the morphology of the CNTs to grow cross-linked CNTs is important when low resistivity is required in a direction parallel to the deposition surface, as is the case for deposition of CNTs into open interconnect trenches as described herein.

Figure 4:
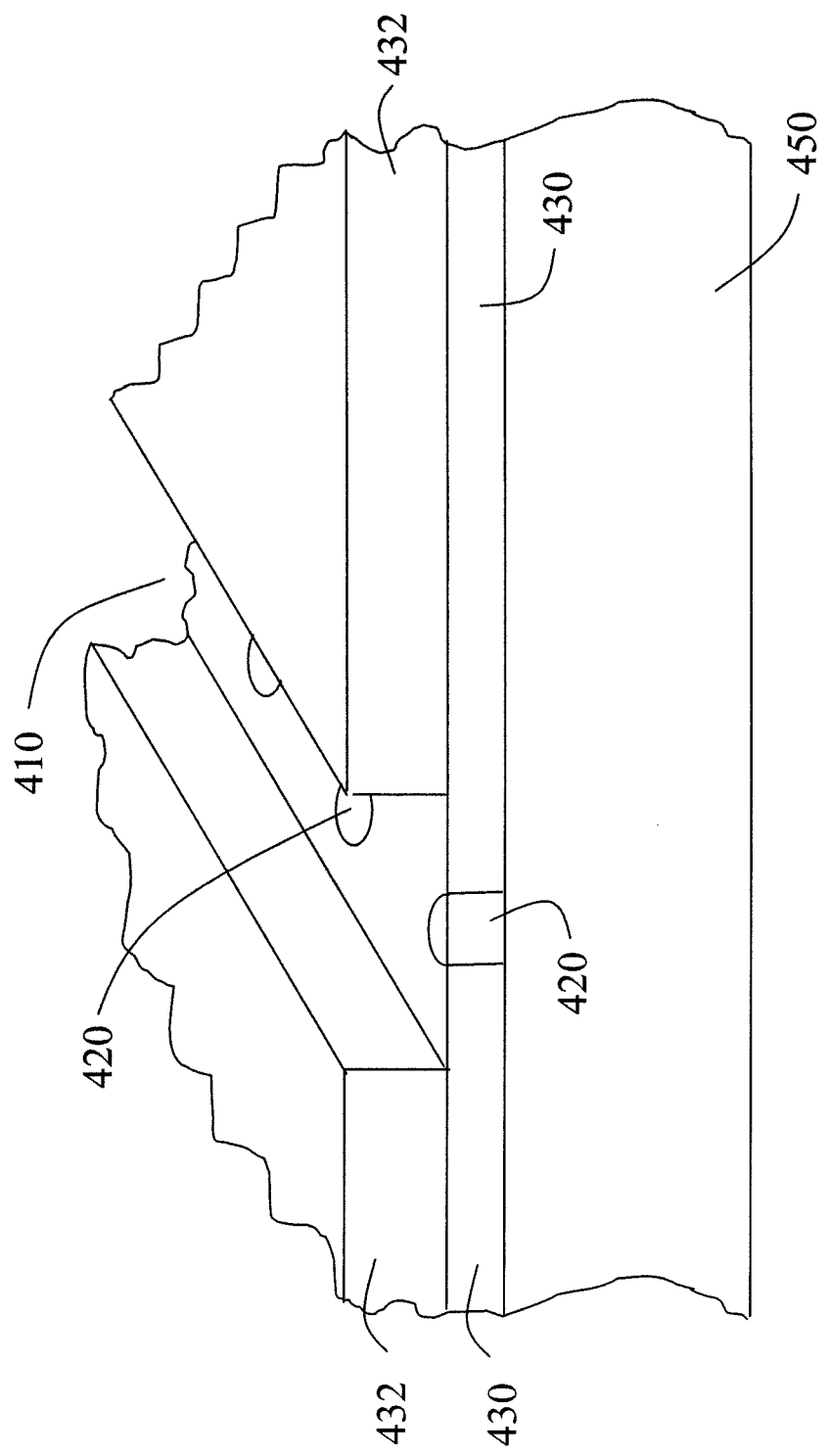
FIG. 4 shows a perspective view of an interconnect trench and filled vias.

FIG. 4 shows a perspective view (features not drawn to scale) of a BEOL interconnect trench 410 formed in a second interlayer dielectric (ILD2) 432 and filled vias 420 in a first interlayer dielectric (ILD1) 430. The vias transmit signals from a semiconductor device below ILD1 up to an interconnect line, which will fill the trench 410, which in turn will transmit the signal in a direction orthogonal to the direction in the via 420. (Consequently, the interconnect line is perpendicular to the longitudinal axis of the via.) Note that the first and second interlayer dielectrics may be ILD1 and ILD2, as described above, on the surface of a substrate 450, the substrate including one or more semiconductor devices, which may be an integrated circuit; however, in other embodiments of the present invention there may be layers of ILD or other materials between the first interlayer dielectric and the substrate. Also note that for the 2× technology node and beyond, the dimensions of vias and interconnect lines in ILD1 and ILD2 will be in the region of 200 Å and less—for example, vias in ILD1 with a diameter of 200 Å and less.

FIGS. 5-9 illustrate steps in the process of forming BEOL interconnect lines comprising cross-linked CNTs for improved signal transmission, according to some embodiments of the present invention. FIG. 10 provides a summary process flow for this single damascene process.

Figure 5:
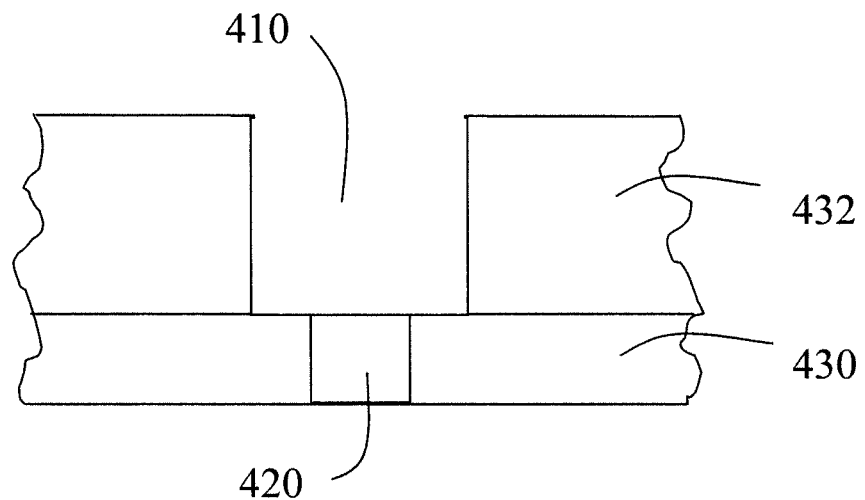
FIG. 5 shows a cross-sectional view of an interconnect trench and filled via, according to some embodiments of the present invention.

FIG. 5 shows a cross-sectional view of an interconnect trench 410 in ILD2 432 and filled via 420 in ILD1 430. The via 420 may be filled with copper or a copper/CNT composite, for example.

Figure 6:
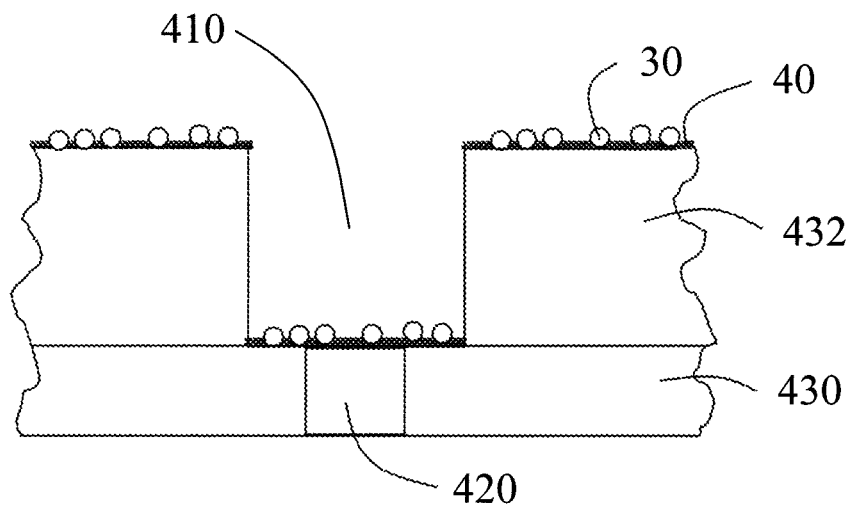
FIG. 6 shows catalyst particles deposited on the surfaces of the structure of FIG. 5, according to some embodiments of the present invention.

FIG. 6 shows catalyst particles 30 deposited on the surfaces of the structure of FIG. 5; although process conditions generally result in minimal deposition on the trench sidewalls. The catalyst particles 30 may be formed of Co and are only 10's or 100's of Angstroms in diameter. (Other examples of catalyst materials are described above.) A barrier layer 40, such as Ta/TiN, may be deposited on the surface prior to catalyst particle deposition. This barrier layer may also act to promote CNT nucleation.

Figure 7:
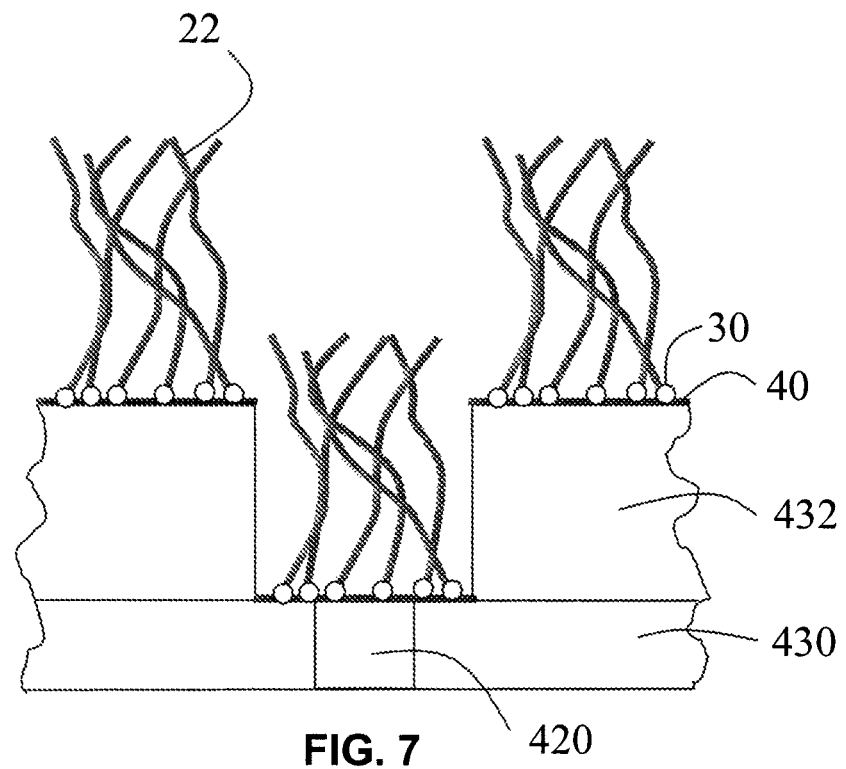
FIG. 7 shows cross-linked CNTs grown on the catalyst coated surfaces of the structure of FIG. 6, according to some embodiments of the present invention.

FIG. 7 shows cross-linked CNTs 22 grown on the catalyst coated surfaces of the structure of FIG. 6. As shown in the figure, the CNTs are grown above the height of the trench. As described above, the deposition conditions are tuned to grow the cross-linked, as opposed to parallel, CNTs.

Figure 8:
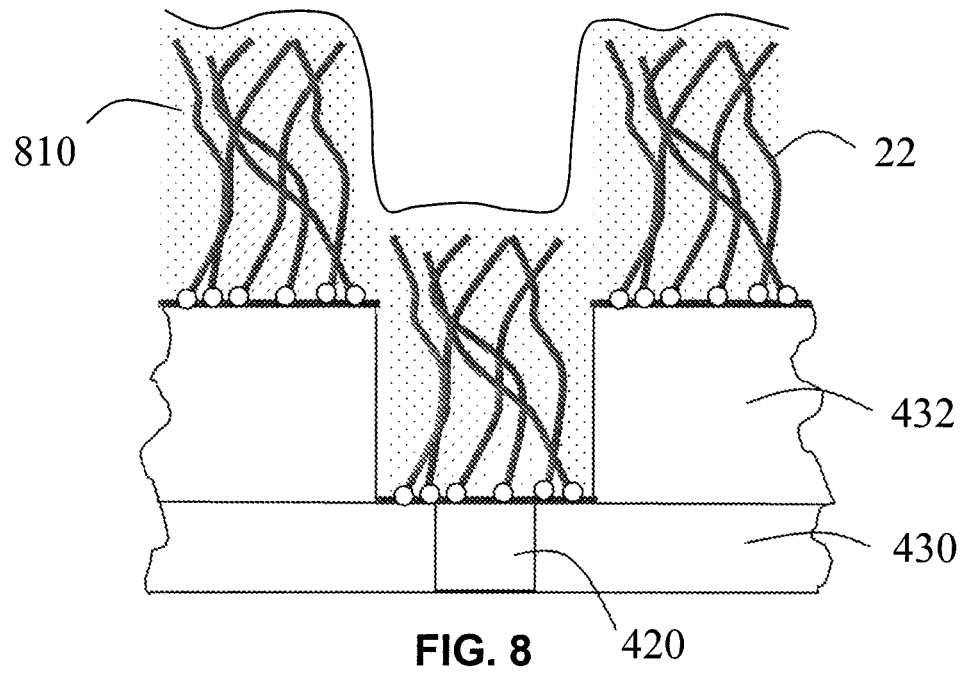
FIG. 8 shows electrodeposited Cu filling the void space between tubes in the structure of FIG. 7, according to some embodiments of the present invention.

FIG. 8 shows electrodeposited Cu 810 filling the void space between tubes in the structure of FIG. 7. Alternatively, CNT composites may be formed with other metals, such as CVD deposited W or Co. Furthermore, some embodiments of the present invention include CNT composites with low-k dielectrics, such as polytetrafluoroethylene (PTFE) which may be deposited using HWCVD. Note that the metals and dielectric materials in the composite serve to encapsulate the CNTs and form a mechanically robust structure.

Figure 9:
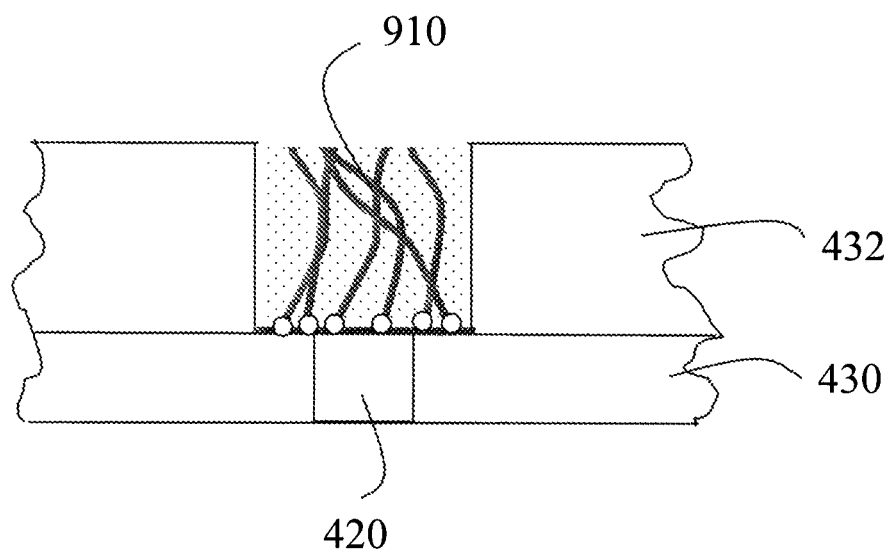
FIG. 9 shows the excess material removed from the structure of FIG. 8, leaving filled trenches with low line resistance, according to some embodiments of the present invention.
Figure 10:
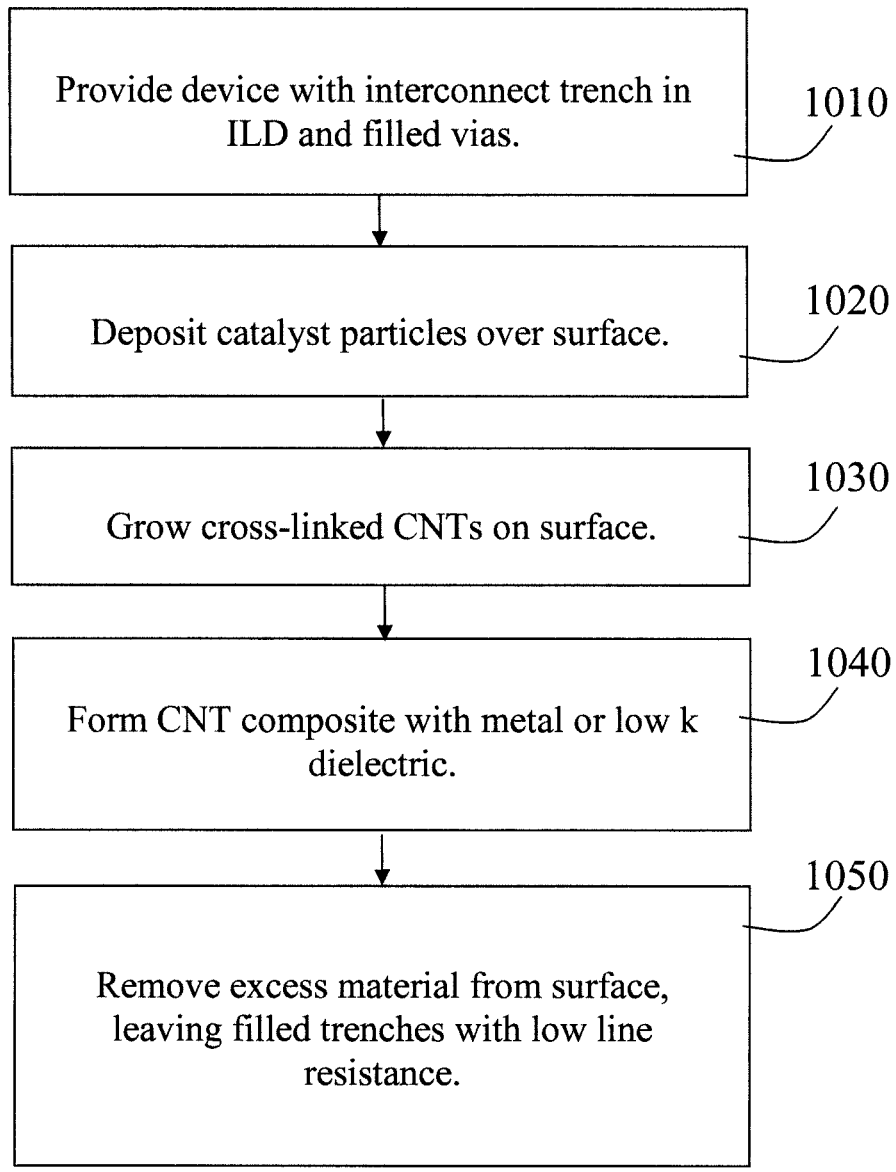
FIG. 10 shows a process flow for a single damascene embodiment of the present invention.

FIG. 9 shows the excess material removed from the structure of FIG. 8, leaving filled trenches with low line resistance. The removal may be done using a chemical mechanical polishing (CMP) process, as is customary in the current Cu damascene processes.

FIG. 10 shows a process flow for a single damascene embodiment of the present invention, as illustrated in FIGS. 5-9. A method of fabricating a BEOL interconnect may comprise the following process steps, executed in the following order. A device is provided with a substrate including a semiconductor device, a first ILD on the surface of the substrate and a second ILD on the first ILD, wherein the first ILD includes one or more filled vias making electrical contact to the semiconductor device and the second ILD includes an interconnect trench running perpendicular to the one or more vias and exposing the one or more vias (1010). Catalyst particles are deposited over the surface of ILD2 and the surface of ILD1 and the one or more vias exposed by the trench (1020). (Furthermore, a barrier layer/nucleation promotion layer may be deposited over the surfaces prior to catalyst deposition.) Cross-linked CNTs are grown on the catalyst particles, the CNTs being grown to a height greater than the depth of the trench (1030). A CNT composite with metal or low-k dielectric is formed by depositing the metal or low-k dielectric in the void space of the cross-linked CNTs (1040). Excess material—the CNT composite, catalyst and barrier layer (if used)—is removed from the top surface of ILD2, leaving a low resistance interconnect line in the trench (1050). Furthermore, the portion of the CNT composite filling the trench which exceeds the height of ILD2 may be removed—providing an interconnect line having a top surface coplanar with the top surface of ILD2.

Although a single damascene process has been described above with reference to the figures, the present invention may be adapted for a dual damascene process. In dual damascene embodiments of the present invention, the CNTs are grown in open vias and trenches at the same time, after which the same process flow is followed as for the single damascene process described above.

Figure 11:
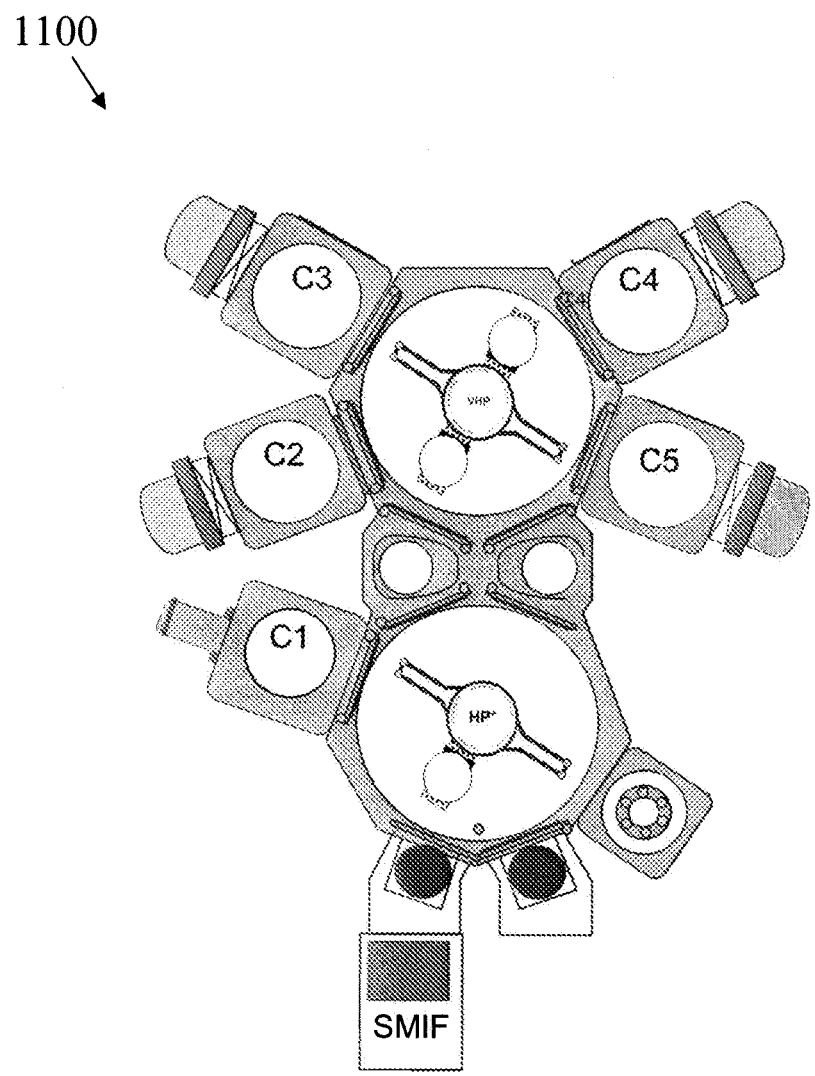
FIG. 11 shows a schematic representation of cluster tool, according to some embodiments of the present invention.

FIG. 11 is a schematic illustration of a processing system 1100 for use in the process described above with reference to FIGS. 5-10. The processing system 1100 includes a standard mechanical interface (SMIF) to a cluster tool equipped with process chambers C1-C5, which may be utilized in the dry deposition process steps described above. For example, the chambers C1-C5 may be configured for the following process steps: catalyst deposition (which may include deposition of an adhesion layer); CNT deposition; and low K dielectric deposition or metal deposition. (Wafers would be transferred out of the cluster tool for processing such as Cu electrodeposition and chemical mechanical polishing.) Examples of suitable cluster tool platforms include Applied Material's Endura™, and Centura™ for smaller substrates. It is to be understood that while a cluster arrangement has been shown for the processing system 1100, a linear system may be utilized in which the processing chambers are arranged in a line without a transfer chamber so that the substrate continuously moves from one chamber to the next chamber.

Figure 12:
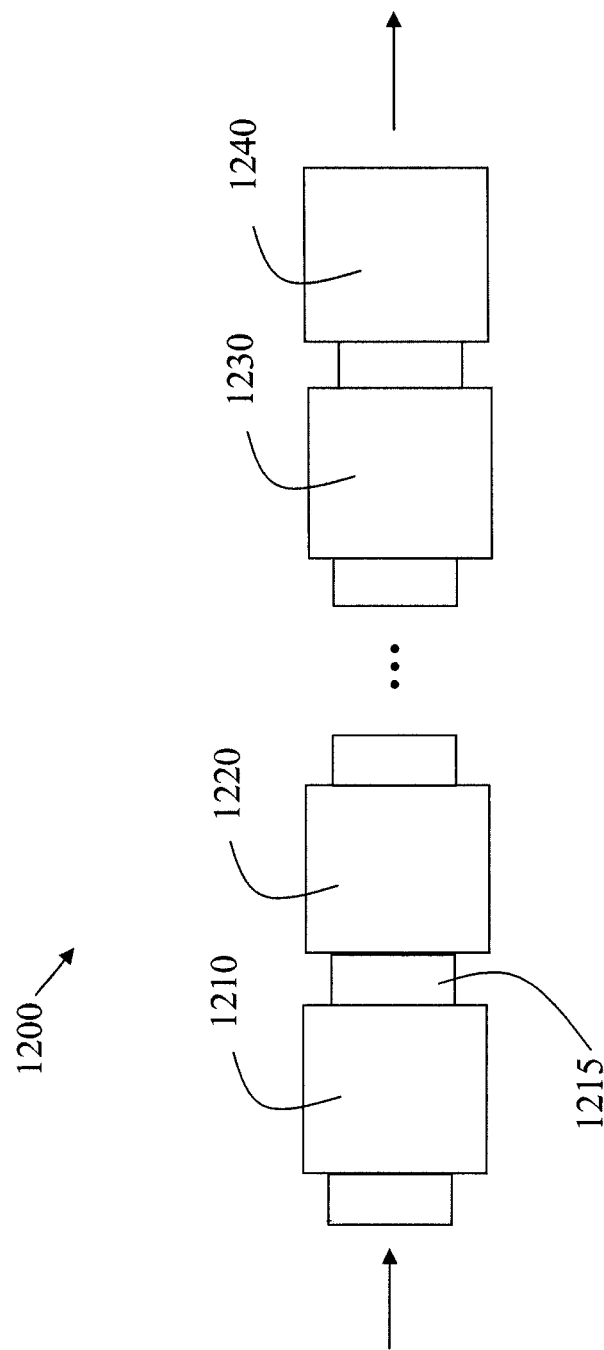
FIG. 12 shows a schematic representation of linear tool, according to some embodiments of the present invention.

FIG. 12 shows a representation of an in-line fabrication system 1200 with multiple in-line tools 1210, 1220, 1230, 1240, etc., according to some embodiments of the present invention. In-line tools may include tools for all of the deposition steps required for the process described above with reference to FIGS. 5-10. Furthermore, the in-line tools may include pre- and post-conditioning chambers. For example, tool 910 may be a pump down chamber for establishing a vacuum prior to the substrate moving through a vacuum airlock 915 into a deposition tool 920. Some or all of the in-line tools may be vacuum tools separated by vacuum airlocks 915. Note that the order of process tools and specific process tools in the process line will be determined by the particular process flow being used—specific examples of which are provided above. Furthermore, substrates may be moved through the in-line fabrication system oriented either horizontally or vertically. A suitable in-line platform for processing tool 1200 may be Applied Materials Aton™.

Although the present invention has been particularly described with reference to the preferred embodiments thereof, it should be readily apparent to those of ordinary skill in the art that changes and modifications in the form and details may be made without departing from the spirit and scope of the invention. It is intended that the appended claims encompass such changes and modifications.

What is claimed is:

1. A method of fabricating an interconnect, comprising:
   providing a substrate including a semiconductor device, a first layer of dielectric over the surface of said substrate and a second layer of dielectric on said first layer of dielectric, wherein said first layer of dielectric includes a filled via making electrical contact to said semiconductor device and said second layer of dielectric including an interconnect trench running perpendicular to the longitudinal axis of said filled via and exposing said filled via;
   depositing catalyst particles over the surface of said second layer of dielectric and the surfaces of said first layer of dielectric and said filled via exposed by said trench;
   growing cross-linked carbon nanotubes on said catalyst particles in a single process, said cross-linked carbon nanotubes being grown directly as cross-linked carbon nanotubes, said cross-linked carbon nanotubes being grown to a height greater than the depth of said trench;
   depositing a material in a void space of said cross-linked carbon nanotubes, forming a carbon nanotube composite; and
   removing said carbon nanotube composite and said catalyst from the top surface of said second layer of dielectric, leaving an interconnect line in said trench
   wherein said growing cross-linked carbon nanotubes comprises growing by chemical vapor deposition in a chamber containing a precursor gas and selecting growth conditions including a partial pressure of precursor gas greater than the transition partial pressure at which carbon nanotube growth transitions from a parallel carbon nanotube growth mode to a cross-linked carbon nanotube growth mode.

2. The method of claim 1, further comprising, prior to catalyst deposition, depositing a barrier layer over the surface of said second layer of dielectric and the surfaces of said first layer of dielectric and said filled via exposed by said trench.

3. The method of claim 2, wherein said removing further comprises removing said barrier layer from the top surface of said second layer of dielectric.

4. The method of claim 2, wherein said barrier layer comprises tantalum.

5. The method of claim 2, wherein said barrier layer comprises titanium nitride.

6. The method of claim 1, wherein said material is a metal.

7. The method of claim 6, wherein said metal is chosen from the group consisting of copper, cobalt and tungsten.

8. The method of claim 6, wherein said metal is electrodeposited.

9. The method of claim 1, wherein said material is a low-k dielectric.

10. The method of claim 1, wherein said removing further comprises removing the portion of said carbon nanotube composite filling said trench which exceeds the height of said second layer of dielectric to provide said interconnect line with a top surface coplanar with the top surface of said second layer of dielectric.

11. A method of fabricating an interconnect, comprising:
providing a substrate including a semiconductor device, a first layer of dielectric over the surface of said substrate and a second layer of dielectric on said first layer of dielectric, wherein said first layer of dielectric includes a via for making electrical contact to said semiconductor device and said second layer of dielectric including an interconnect trench running perpendicular to the longitudinal axis of said filled via and exposing said filled via;
depositing catalyst particles over the surface of said second layer of dielectric and the surfaces of said first layer of dielectric and said semiconductor device exposed by said via;
growing cross-linked carbon nanotubes on said catalyst particles in a single process, said cross-linked carbon nanotubes being grown directly as cross-linked carbon nanotubes, said cross-linked carbon nanotubes being grown to a height greater than the depth of said trench;
depositing a material in a void space of said cross-linked carbon nanotubes, forming a carbon nanotube composite; and
removing said carbon nanotube composite and said catalyst from the top surface of said second layer of dielectric, leaving a filled via and an interconnect line in said trench
wherein said growing cross-linked carbon nanotubes comprises growing by chemical vapor deposition in a chamber containing a precursor gas and selecting growth conditions including a partial pressure of precursor gas greater than the transition partial pressure at which carbon nanotube growth transitions from a parallel carbon nanotube growth mode to a cross-linked carbon nanotube growth mode.

12. The method of claim 11, wherein said material is a metal.

13. The method of claim 11, wherein said material is a low-k dielectric.

14. The method of claim 1, wherein said precursor gas is selected from the group consisting of xylene and ethanol.

15. The method of claim 11, wherein said precursor is selected from the group consisting of xylene and ethanol.

* * * * *